US008288416B2

(12) United States Patent
Patil et al.

(10) Patent No.: US 8,288,416 B2
(45) Date of Patent: Oct. 16, 2012

(54) SUBSTITUTED PIPERIDINOPHENYL OXAZOLIDINONES

(75) Inventors: Vijaykumar Jadgishwar Patil, Solapur (IN); Mahesh Vithalbhai Patel, Aurangabad (IN); Bharat Kalidas Trivedi, Aurangabad (IN); Deepak Vijaykumar Dekhane, Pune (IN); Mohammad Usman Shaikh, Ahmednagar (IN); Yati Chugh, Panchkula (IN); Rajesh Prabhakar Chavan, Jalgaon (IN); Mohammad Alam Jafri, Aurangabad (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 485 days.

(21) Appl. No.: 12/311,243

(22) PCT Filed: Sep. 22, 2007

(86) PCT No.: PCT/IB2007/002758
§ 371 (c)(1),
(2), (4) Date: Dec. 28, 2009

(87) PCT Pub. No.: WO2008/038092
PCT Pub. Date: Apr. 3, 2008

(65) Prior Publication Data
US 2010/0120721 A1    May 13, 2010

(30) Foreign Application Priority Data
Sep. 25, 2006    (IN) .......................... 1526/MUM/2006

(51) Int. Cl.
*A61K 31/445*    (2006.01)
*C07D 413/14*    (2006.01)
(52) U.S. Cl. ......................................... 514/326; 546/21
(58) Field of Classification Search .................. 514/326; 546/21
See application file for complete search history.

(56) References Cited

U.S. PATENT DOCUMENTS

| 5,668,286 | A  | * | 9/1997 | Yamada et al. | ............... | 546/209 |
| 7,687,627 | B2 | * | 3/2010 | Deshpande et al. | ............ | 546/19 |
| 2009/0018123 | A1 | * | 1/2009 | Sindkhedkar et al. | ..... | 514/227.8 |
| 2010/0056581 | A1 | * | 3/2010 | Patel et al. | .................... | 514/340 |
| 2010/0144735 | A1 | * | 6/2010 | Deshpande et al. | ....... | 514/236.8 |

FOREIGN PATENT DOCUMENTS

| WO | WO95/25106 A1 | 9/1995 |
| WO | WO0140236 A2 | 6/2001 |
| WO | WO2004048350 A2 | 6/2004 |
| WO | WO 2005113520 A1 | 12/2005 |
| WO | WO2007/132314 | * 11/2007 |

OTHER PUBLICATIONS

Bungaard "Design of prodrug . . ." p. 1-3 (1985 ).*
Wakefield "Fluorinated pharmaceuticals" Innovations in Pharmaceutical Technology v. 74, p. 76-78 (2003.*

* cited by examiner

*Primary Examiner* — Celia Chang
(74) *Attorney, Agent, or Firm* — Bio Intellectual Property Serives LLC; O. M. (Sam) Zaghmout

(57) ABSTRACT

The present invention relates to oxazolidinones of Formula I and pharmaceutically acceptable salts, pharmaceutically acceptable solvates or polymorphs thereof. The invention also relates to processes for the preparation of the compound of Formula I and pharmaceutically acceptable salts, pharmaceutically acceptable solvates or polymorphs thereof, and to pharmaceutical compositions containing the compounds of Formula I and pharmaceutically acceptable salts, pharmaceutically acceptable solvates or polymorphs thereof and to methods for treating or preventing microbial infections using the compounds of Formula I and pharmaceutically acceptable salts, pharmaceutically acceptable solvates or polymorphs thereof.

14 Claims, No Drawings

SUBSTITUTED PIPERIDINOPHENYL OXAZOLIDINONES

FIELD OF THE INVENTION

The present invention relates to certain substituted piperidinophenyl oxazolidinones having antimicrobial activity. The invention further relates to pharmaceutical compositions containing the compounds of the present invention and methods of treating microbial infections with the compounds of the present invention.

The invention also relates generally to processes for the preparation of the substituted piperidinophenyl oxazolidinone compounds, pharmaceutically acceptable salts, pharmaceutically acceptable solvates and polymorphs thereof.

BACKGROUND OF THE INVENTION

Oxazolidinones represent a novel chemical class of synthetic antimicrobial agents. Linezolid represents the first member of this class to be used clinically. Oxazolidinones display activity against important Gram-positive human and veterinary pathogens including methicillin-resistant *Staphylococcus aureus* (MRSA), vancomycin resistant enterococci (VRE) and β-lactam resistant *Streptococcus pneumoniae* (PRSP). There are several patents cited in the literature, which refer to oxazolidinones having antibacterial activity. The substituted piperidinophenyl oxazolidinones are disclosed in PCT application Nos. WO 95/25106, WO 96/13502, WO 04/007488, WO 04/007489, WO 05/054234 and PCT/IB2007/001179.

DESCRIPTION OF THE INVENTION

In one general aspect there is provided oxazolidinone compounds having the structure of Formula I

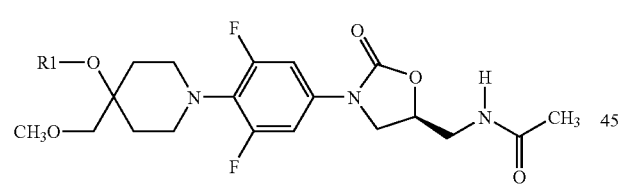

Formula I and pharmaceutically acceptable salts, pharmaceutically acceptable solvates or polymorphs thereof,
wherein
$R_1$ is
a) $COR_a$,
b) $PO(OH)_2$ or

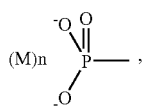

c) amino acid residue attached via carbonyl of the amino acid, the amino acid residue is selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine or the optically active isomers thereof or the racemic mixtures thereof, wherein
$R_a$ is $C_1$-$C_6$ alkyl and $C_1$-$C_6$ alkyl substituted with hydroxyl, COOH, amine or halogen;
M is a monovalent or a divalent cation selected from $Na^+$, $K^+$, $Mg^{2+}$, or $Ca^{2+}$; and
n is 2 for a monovalent cation or n is 1 for a divalent cation.

In another aspect there are provided processes for preparing the compounds of invention of Formula I and their pharmaceutically acceptable salts, pharmaceutically acceptable solvates and polymorphs.

In another aspect there are provided pharmaceutical compositions comprising the compounds of Formula I and pharmaceutically acceptable salts, pharmaceutically acceptable solvates or polymorphs thereof In yet another aspect there are provided methods of treating or preventing microbial infections using the compound of Formula I and pharmaceutically acceptable salts, pharmaceutically acceptable solvates or polymorphs thereof.

Representative compounds of the invention are:
Phosphoric acid mono-(1-{4-[(S)-5-(acetylamino-methyl)-2-oxo-oxazolidin-3-yl]-2,6-difluorophenyl}-4-methoxymethyl-piperidin-4-yl)ester;
Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester di sodium salt;
Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester di potassium salt;
Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester magnesium salt;
Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester calcium salt;
Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester arginine salt;
Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester lysine salt;
1-{4-[(S)-5-(Acetylamino-methyl)-2-oxo-oxazolidin-3-yl]-2,6-difluoro-phenyl}-4-methoxymethyl-piperidin-4-yl acetate;
2-Amino-acetic acid 1-{4-[(S)-5-(acetylamino-methyl)-2-oxo-oxazolidin-3-yl]-2,6-difluoro-phenyl}-4-methoxymethyl-piperidin-4-yl ester;
2-Amino-propionic acid 1-{4-[(S)-5-(acetylamino-methyl)-2-oxo-oxazolidin-3-yl]-2,6-difluoro-phenyl}-4-methoxymethyl-piperidin-4-yl ester hydrochloride salt;
2-Amino-propionic acid 1-{4-[(S)-5-(acetylamino-methyl)-2-oxo-oxazolidin-3-yl]-2,6-difluoro-phenyl}-4-methoxymethyl-piperidin-4-yl ester triflouroacetic acid salt;
2-Amino-3-methyl butyric acid 1-{4-[(S)-5-(acetylamino-methyl)-2-oxo-oxazolidin-3-yl]-2,6-difluoro-phenyl}-4-methoxymethyl-piperidin-4-yl ester;
4-{[1-{4-[(5S)-5-(acetylaminomethyl)-2-oxo-1,3-oxazolidin-3-yl]-2,6-difluorophenyl}-4-(methoxymethyppiperidin-4-yl]oxy}-4-oxobutanoic acid;
2-Amino-acetic acid 1-{4-[(S)-5-(acetylamino-methyl)-2-oxo-oxazolidin-3-yl]-2,6-difluorophenyl}-4-methoxymethyl-piperidin-4-yl ester hydrochloride salt;

2-Amino-acetic acid 1-{4-[(S)-5-(acetylamino-methyl)-2-oxo-oxazolidin-3-yl]-2,6-difluorophenyl}-4-methoxymethyl-piperidin-4-yl ester triflouroacetic acid salt; and 2-Amino-3,3-dimethylpropionic acid 1-{4-[(S)-5-(acetylamino-methyl)-2-oxo-oxazolidin-3-yl]-2,6-difluorophenyl }-4-methoxymethyl-piperidin-4-yl ester methane sulfonic acid salt.

The phrase "pharmaceutically acceptable salt" as used herein refers to one or more salts of the free base of the invention which possess the desired pharmacological activity of the free base and which are neither biologically nor otherwise undesirable. The salts are suitable for use in contact with the tissues of human and lower animals without undue toxicity, irritation, allergic response and the like, and are commensurate with a reasonable benefit/risk ratio. Pharmaceutically acceptable salts are well known in the art. For example, S. M. Berge, et. al. describe pharmaceutically acceptable salts in detail in *J. Pharmaceutical Sciences,* 66: 1-19 (1977), incorporated herein by reference. The salts can be prepared in situ during the final isolation and purification of the compounds of the invention, or separately by reacting the free base function with a suitable acid. These salts may be obtained from inorganic or organic acids. Examples of inorganic acids include hydrochloric acid, nitric acid, perchloric acid, hydrobromic acid, sulphuric acid or phosphoric acid. Examples of organic acids include acetic acid, propionic acid, oxalic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulphonic acid, p-toluene sulphonic acid, salicyclic acid and the like. Also, included are the salts with various amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof or dipeptides, tripeptides and polypeptides derived from the monoaminoacid units thereof.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malonate, 2-naphthalenesulfonate, nicotinate, oleate, palmitate, pamoate, pectinate, persulfate, 3-phenylpropionate, phosphate, picrate, pivalate, propionate, stearate, sulfate, tartrate, thiocyanate, p-toluenesulfonate, undecanoate, valerate salts, and the like.

Salt of an acid moiety in the compound can also be prepared by reacting with a suitable base. These suitable salts are furthermore those of the inorganic or organic bases. Inorganic bases such as KOH, NaOH, Ca(OH)$_2$, Al(OH)$_3$. The organic base salts from basic amines such as ethylamine, triethylamine, diethanolamine, ethylenediamine, guanidine or heterocyclic amines such as piperidine, hydroxyethylpyrrolidine, hydroxyethylpiperidine, morpholine, piperazine, N-methyl piperazine, and the like or basic amino acids such as optically pure and racemic isomers of arginine, lysine, histidine, tryptophan, and the like.

Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

"Therapeutically effective amount" means that amount of active compound(s) or pharmaceutical agent(s) that elicit the biological or medicinal response in a tissue system, animal or human sought by a researcher, veterinarian, medical doctor or other clinician, which response includes alleviation of the symptoms of the disease or disorder being treated. The specific amount of active compound(s) or pharmaceutical agent (s) needed to elicit the biological or medicinal response will depend on a number of factors, including but not limited to the disease or disorder being treated, the active compound(s) or pharmaceutical agent(s) being administered, the method of administration, and the condition of the patient.

The term "treatment" unless otherwise indicated, includes the treatment or prevention of a microbial infection as provided in the method of the present invention.

As used herein, unless otherwise indicated, the term "microbial infection(s)" includes bacterial infections and protozoa infections which occur in human or animals including mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C-F (minute-colony streptococci), viridans streptococci, *Corynebacterium minutissimum, Clostridium* spp., or *Bartonella henselae;* uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chiamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare;* gastroenteritis related to infection by *Campylobacter jejuni;* intestinal protozoa related to infection by *Cryptosporidium* spp.; odontogenic infection related to infection by viridans streptococci; persistent cough related to infection by *Bordetella pertussis;* gas gangrene related to infection by *Clostridium perfringens* or *Bacteroides* spp.; and atherosclerosis related to infection by *Helicobacter pylori* or *Chlamydia pneumoniae.* Bacterial infections and protozoa infections and disorders related to such infections that may be treated or prevented in animals include the following: bovine respiratory diseases related to infection by *P. haem.*, *P. multocida*, *Mycoplasma bovis*, or *Bordetella* spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae, Klebsiella* spp., *Corynebacterium,* or *Enterococcus* spp.; swine respiratory disease related to infection by *A. pleuro., P. multocida,* or *Mycoplasma* spp.; swine enteric disease related to infection by *E. coli, Lawsonia intracellularis, Salmonella,* or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius,* coagulase neg. Staph. or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas,* or *Prevotella*.

The compounds of Formula I and pharmaceutically acceptable salts, pharmaceutically acceptable solvates or polymorphs thereof possess pharmacokinetic parameters suitable for once a day dosing. The compounds of Formula I and pharmaceutically acceptable salts, pharmaceutically acceptable solvates or polymorphs thereof, show good water solubility which makes them suitable for an IV, and IM formulations. Thus, the compounds of Formula I and pharmaceutically acceptable salts, pharmaceutically acceptable solvates or polymorphs thereof, can be formulated into oral, IV, and IM formulations.

Another aspect relates to methods of preparation of the compounds of Formula I and pharmaceutically acceptable salts, pharmaceutically acceptable solvates or polymorphs thereof. The starting materials may be prepared by methods known in the art such as U.S. Pat. No. 5,668,286, PCT application WO 2004/007489, PCT application WO 2005/054234 or by procedures that would be well known to one of ordinary skill in the art of synthetic organic chemistry.

The following abbreviation are used in the text: DCM for dichloromethane, DMAP for 4-dimethylaminopyridine, DMF for N,N-dimethylformamide, DMSO for dimethyl sulfoxide, EtOAc for ethyl acetate, TEA for triethylamine, THF for tetrahydrofuran, $Ac_2O$ for acetic anhydride, PPTS for pyridinium tosylate, PTSA for para-toluene sulfonic acid, LDA for lithium diisopropylamine, DCC for N,N'-dicyclohexyl carbodiimide, EEDQ for N-ethoxycarbonyl-2-ethoxy-1,2-dihydroquinoline, EDCI for 1-(3-dimethylaminopropyl)-3-ethyl carbodiimide hydrochloride.

The term "halogenated solvents" refers to solvents containing one or more halogen atom for example dichloromethane, chloroform, carbon tetrachloride, ethylene dichloride and the like. The term "ester coupling reagent" refers to reagents which are act as activating groups and help in formation of an ester linkage. For example DCC, EDCI, 2,4,6-trichlorobenzoyl chloride, pentafluorophenol (PFP).

As shown in Scheme 1, (S)-N-{3-[3,5-difluoro-4-(4-methoxymethyl-4-hydroxypiperidine-1yl)phenyl]-2-oxo-oxazolidin-5-yl methyl}-acetamide (Formula II) can be treated with a phosphoramidite such as dibenzyl-N,N,diisopropylphosphoramidite, dimethyl-N,N,diisopropylphosphoramidite, diethyl-N,N,diisopropylphosphoramidite, diallyl-N,N,diisopropyl phosphoramidite, di-t-butyl-N,N,diisopropylphosphoramidite, and the like, in a suitable solvent such as dichloromethane, chloroform, acetonitrile, ethyl acetate in presence of a suitable activating agent such as tetrazole, trimethyl silyl chloride, pyridinium hydrochloride, pyridinium trifluoroacetate, 4,5-dicyanoimidazole, pyridinium trifluomethanesulfonate, pyridinium acetate, pyridinium chloroacetate, pyridinium dichloro acetate, polyvinyl pyridinium hydrochloride, 2-amino-4,6-dimethyl pyrimidinium trifluoroacetate, imidazolium hydrochloride, imidazolium trifluoroacetate, aniline hydrochloride, p-anisidine trifuoroacetate, o-toluidine hydrochloride, p-toluidine hydrochloride, phenanthrene trifluoroacetate, followed by the addition of a suitable oxidizing agent such as hydrogen peroxide (30%, 50% or 90%), urea hydrogen peroxide, peracetic acid, per trifluoroacetic acid, iodobenzene diacetate, m-chloroperbenzoic acid, and the like. The reaction mixture can be stirred at a temperature in the range of −20 to +50° C. for a period of 0.5 to 8 h to obtain compound of Formula III. Alternatively, the compound of Formula III can be obtained by treating a compound of Formula II with $PCl_3$, in the presence of any of the above mentioned activating agents followed by the addition of a suitable alcohol such as benzyl alcohol, propane diol, 2,2-dimethyl-1,3-propane diol, and the like, in the presence of a base like triethylamine, N-ethyl diisopropyl amine or diisopropyl amine followed by oxidation with any one of the oxidizing agents mentioned above.

The protecting groups of the compound of Formula III may be removed by using hydrogenation using a catalyst such as 5% palladium on carbon, 10% palladium on carbon, 20% palladium hydroxide on carbon in a suitable solvent such as halogenated solvents like dichloromethane, chloroform, ethylene dichloride; methanol, ethanol, tetrahydrofuran and mixtures thereof including aqueous mixtures at room temperature for 1 to 24 h to obtain compound of Formula IV.

The compound of Formula IV may be further treated with a base such as sodium hydroxide, potassium hydroxide, calcium hydroxide, or magnesium hydroxide, in an organic solvent to afford the compound of Formula V. Similarly, on treatment with a suitable amino acid compound of Formula III afforded compound of Formula V.

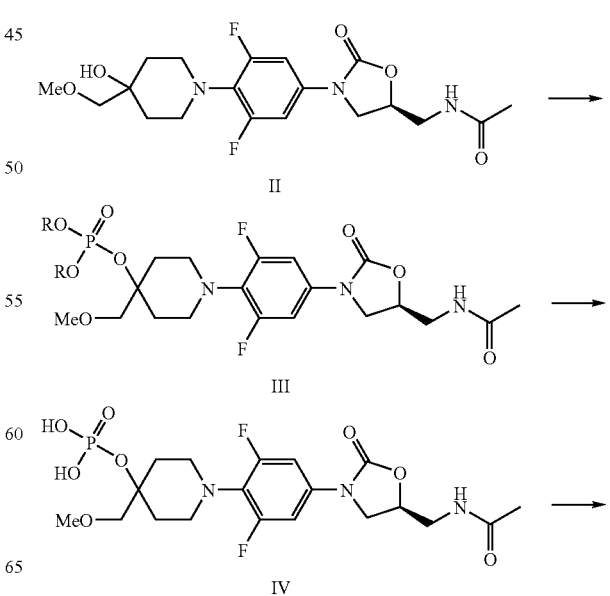

-continued

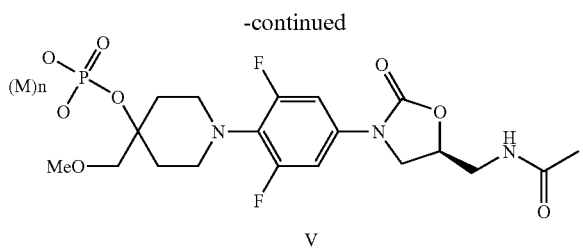

V

As shown in Scheme 2, a compound of Formula II can be converted to compound of Formula I by treating with a suitable acid such as amino acid, succinic acid or substituted acids in the presence of an ester coupling reagent such as DCC, trichlorobenzoyl chloride, EEDQ in an organic solvent such as tetrahydrofuran, halogenated solvents, DMF, and mixtures thereof.

Scheme-2

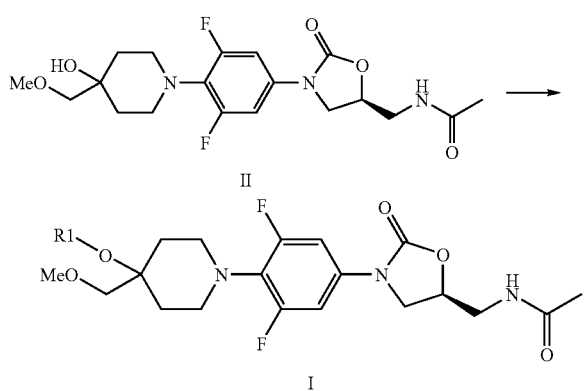

The oxazolidinone antibacterial agents of Formula I and pharmaceutically acceptable salts, pharmaceutically acceptable solvates or polymorphs thereof, have potential for treatment of Gram-positive infections including those which result from multi-resistant strains. These compounds are useful for the treatment of Gram-positive or Gram-negative microbial infections in humans and veterinary pathogens including Linezolid-resistant strains. The infections can be treated by parenteral, intra-muscular, oral or topical administration. The infection in human and other warm-blooded animals can be systemic or topical.

Examples of infections that may be treated with the compounds of the present invention include central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. Specifically, infectious diseases that may be treated with the compounds of the present invention are gram-positive infections such as osteomyelitis, endocarditis and diabetic foot.

The compounds described herein are useful for the treatment or prophylaxis of Gram-positive or Gram-negative microbial infections in humans and other warm-blooded animals. The oxazolidinone antibacterial compounds of this invention are useful for treatment of Gram-positive infections including those, which result from multi-resistant strains. The compounds of this invention are useful antimicrobial agents effective against various humans and veterinary pathogens specially included linezolid-resistant strains.

In contrast to linezolid, the compounds described herein demonstrate bactericidal activity against different resistant microorganisms and in particular different strains of *Enterococcus faecalis*. In addition they display activity against linezolid-resistant *S. aureus* strains, linezolid-resistant *E. faecalis* strains and in particular linezolid-resistant *S. pneumoniae* strains.

The infection in human and other warm-blooded animals can be systemic or topical. The compounds of this invention may be used to prevent infections caused by Gram-positive and Gram-negative bacteria by administering the compound to a subject that is at risk for developing an infection caused by Gram-positive or Gram-negative bacteria. A subject at risk for developing an infection may be a health care worker, surgical patient, immune-comprised or the like.

One aspect encompasses certain compounds, compositions, dosage forms, and methods of administering the compounds to a human or other animal subject. In an another aspect, the pharmaceutical compositions contain an effective amount of the compounds of Formula I or salts thereof described in this specification in admixture with a pharmaceutically acceptable carrier, diluent or excipients, and optionally other therapeutic ingredients. Specific compounds, compositions and dosage forms to be administered must, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio. The pharmaceutical compositions are prepared according to conventional procedures used by persons skilled in the art to make stable and effective compositions. In the dosage forms, an effective amount of the active compound or the active ingredient is any amount, which produces the desired results. An effective amount can also be that amount of the active compound or active ingredient that will elicit the biological or medical response that is being sought.

For the purpose of this invention, a pharmaceutical composition will contain one or more of the active compounds of the invention salts, and/or hydrates thereof, in a form to be administered alone, but generally in a form to be administered in admixture with a pharmaceutical carrier selected with regard to the intended route of administration and standard pharmaceutical practice. Suitable carriers which can be used are, for example, diluents or excipients such as fillers, extenders, binders, emollients, wetting agents, disintegrants, surface active agents and lubricants which are usually employed to prepare such drugs depending on the type of dosage form.

The compounds and compositions can be administered to a human or other animal by any suitable route of administration including, for example, oral, rectal, vaginal, parenteral (subcutaneous, intramuscular, intravenous), transdermal, topical and like. Dosage forms include solutions, suspensions, tablets, pills, powders, troches, dispersions, suspensions, emulsions, solutions, pellets, gels, granules, capsules, injectable preparations, patches, ointments, creams, liniments, salves, cachets, aerosol sprays, lotions, shampoos and the like.

The prophylactic or therapeutic dose of the compound of Formula I and pharmaceutically acceptable salts, pharmaceutically acceptable solvates or polymorphs thereof, in the prevention, acute or chronic management of infection or disease will vary depending on one or more factors which include but are not limited to the severity of condition to be treated, the risk and the route of administration. In addition, the dose, and perhaps the dose frequency, will also vary according to the age, sex, body weight and response of the individual patient. In general, the total daily dose range, for the compounds of Formula I and salts thereof, for the conditions described herein, is from about 200 mg to 1800 mg or more, in single or divided doses. While parenteral administration may be a single dose or up to 3 divided doses, intravenous administration can include a continuous drip.

The term "an amount sufficient to eradicate such infections but insufficient to cause undue side effects" is encompassed by the above-described dosage amount and dose frequency schedule.

A specific embodiment of the invention is that based on the pharmacokinetic profile of compounds the compounds can be administered once-a-day.

The pharmaceutical compositions of the present invention suitable for oral administration may be presented as discrete units, for example, such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

The compositions of the present invention include compositions such as suspensions, solutions, elixirs, aerosols, injectables and solid dosage forms. Carriers as described in general below are commonly used in the case of oral solid preparations (such as powders, capsules and tablets). Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic acid salts, boric acid powder, polyethylene glycol and solid polyethylene glycol. The tablet, can be coated, and made into sugar-coated tablets, gelatin-coated tablets, enteric-coated tablets, film-coated tablets, or tablets comprising two or more layers. Tablets may be coated by standard aqueous or non-aqueous techniques. In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar. Desirably, each oral dosage form contains from about 200 mg to about 2500 mg of the active ingredient. In molding the pharmaceutical composition into a suppository form, a wide variety of carriers known in the art can be used. Examples of suitable carriers include polyethylene glycol, cacao butter, higher alcohols, gelatin, and semisynthetic glycerides.

The composition can be administered parenterally by intramuscular, intravenous or subcutaneous administration by parenteral dosages. Parenteral dosages may be in the form of ready to use dosage forms or solutions for parenteral dosage may be diluted prior to its use. When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

Another route of administration is topically, for which creams, ointments, shampoos, lotions, dusting powders, and the like are well suited. Generally, an effective amount of the compound of present invention in a topical form is from about 0.1% w/w to about 10% w/w of the total composition. Topical application may be as a non-sprayable form, viscous to semi-solid or solid forms comprising a carrier compatible with topical application. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient in combination with a solid or liquid inert carrier material. In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

Another aspect is the preparation of storage stable compositions of the compounds of the invention of Formula I. Such stable compositions can be advantageously made through the use of selective stabilizers. Different stabilizers are known to those skilled in the art of making pharmaceutical compositions. Of special utility for making storage stable compositions of the compound of the invention of Formula I, stabilizers such as disodium ethylenediaminetetraacetic acid (EDTA), tromethamine, cyclodextrins such as gamma-cyclodextrin, hydroxy-propyl-gamma-cyclodextrin have been found to be useful.

The antimicrobial pharmaceutical composition may further contain ordinary dissolving aids, buffers, pain-alleviating agents, and preservatives, and optionally coloring agents, perfumes, flavors, sweeteners, and other drugs.

Following examples illustrate the methods of preparation of the compounds of the invention and are provided only as examples, but not to limit the scope of the compounds of invention.

Starting material (S)-N-{3-[3,5-difluoro-4-(4-methoxymethyl-4-hydroxypiperidine-1yl)-phenyl]-2-oxo-oxazolidin-5-yl methyl}-acetamide was prepared using procedure described in PCT application PCT/IB/2007/001179.

EXAMPLE 1

(S)—N-{3-[3,5-Difluoro-4-(4-methoxymethyl-4-di-O-benzylphosphoryloxy-piperidin-1yl)-phenyl]-2-oxo-oxazolidin-5-ylmethyl}-acetamide To a solution of (S)—N-{3-[3,5-difluoro-4-(4-methoxymethyl-4-hydroxypiperidine-1yl)-phenyl]-2-oxo-oxazolidin-5-yl methyl}-acetamide (0.2 mmol) and tetrazole (0.6 mmol) in dichloromethane (5 ml) was added dibenzyl N,N,diisopropylphosphoramidite (0.4 mmol) and the resulting mixture was stirred for 4 h. The resulting solution was cooled to 0° C. and 0.6 ml of 0.5M m-chloroperbenzoic acid solution in dichloromethane was added. After 4 h, the solvent was evaporated under residue pressure and the residue chromatographed on a column of silica gel to obtain the product as a off-white solid in 75% yield, M.F. $C_{33}H_{38}F_2N_3O_8P$; M+1=674.

EXAMPLE 2

(S)—N-{3-[3,5-Difluoro-4-(4-(S)-2-tert-Butoxycarbonylamino-propionyl-4-methoxymethyl-piperidine-1-yl)phenyl]-2-oxo-oxazolidin-5-yl methyl}-acetamide To a solution of (S)—N-{3-[3,5-difluoro-4-(4-methoxymethyl-4-hydroxypiperidine-1yl)-phenyl]-2-oxo-oxazolidin-5-yl methyl}-acetamide (4.1 g, 21.69 mmol) of N-Boc-alanine in dichloromethane (30 ml), under argon, was added DCC (4.2 g, 21.7 mmol), at 0-5° C. The resulting mixture was stirred for 0.5 h. To this solution, N—{(S)-3-[3,5-Difluoro-4-(4-hydroxy-4-methoxymethyl-piperidin-1-yl)phenyl]-2-oxo-oxazolidin-5-ylmethyl}-acetamide, (3 g, 7.2 mmol) and DMAP (2.52 g, 21.7 mmol) were added successively. The reaction mass stirred at room temperature for 15-20 hrs. The reaction mixture was filtered under suction and the residue further washed with additional dichloromethane (50 ml). The filtrate was washed with water (100 ml×2), dried over sodium sulfate, and the solvent evaporated under reduced pressure. The residue was chromatographed on a column of silica gel to obtain the product as a white hygroscopic, solid, 0.5 g, in 12% yield. MF=$C_{27}H_{38}F_2N_4O_8$; Mass: 585 (M+1).

EXAMPLE 3

Phosphoric acid mono-(1-{4-[(S)-5-(acetylamino-methyl)-2-oxo-oxazolidin-3-yl]-2,6-difluorophenyl}-4-methoxymethyl-piperidin-4-yl)ester To a suspension of (S—N-{3-[3,5-difluoro-4-(4-methoxymethyl-4-di-O-benzylphosphoryl-oxypiperidine-1yl)phenyl]-2-oxo-oxazolidin-5-yl methyl}-acetamide (0.15 mmol) and 20% palladium hydroxide (20 mg) in 20 ml of a mixture of dichloromethane/aqueous methanol was stirred at room temperature for 6 h. The catalyst was filtered and the residue evaporated under reduced pressure. The residue obtained was triturated with acetone to obtain a white solid as product in 70% yield. Mp.>140° C.; M.F.: $C_{19}H_{26}F_2N_3O_8P$; M+1=493. Aqueous solubility >200 mg/ml.

EXAMPLE 4

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester di sodium salt To a solution of phosphoric acid mono-(1-{4-[(S)-5-(acetylamino-methyl)-2-oxo-oxazolidin-3-yl]-2,6-difluorophenyl}-4-methoxymethyl-piperidin-4-yl) ester (5.0 g, 0.010 mol) anhydrous methanol (50 ml) at 0-5° C., under argon, was added anhydrous sodium methoxide powder (0.542 g, 0.010 mol). The reaction mixture was stirred at 5-10° C. for 2 hours. The ice-bath was removed and the stirring continued further at 30-35° C. for 1 hour. The reaction mixture was filtered and the filtrate evaporated under reduced pressure. Acetone (25 ml) was added to the residue and triturated. The solvent was decanted. This procedure was repeated twice with acetone (50 ml). Acetone after the third trituration was decanted and the residue dried under reduced pressure to obtain the product as off-white solid, 5.0 g, in 92% yield, Mp>150° C. (dec); MF: $C_{19}H_{24}F_2K_2N_3O_8P$. Aqueous solubility at pH 7 was >200 mg/ml.

EXAMPLE 5

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester di potassium salt To a solution of phosphoric acid mono-(1-{4-[(S)-5-(acetylamino-methyl)-2-oxo-oxazolidin-3-yl]-2,6-difluorophenyl}-4-methoxymethyl-piperidin-4-yl) ester (5.0g, 0.010mol) anhydrous methanol (50 ml) at 0-5° C., under argon, was added anhydrous potassium carbonate (1.38 gm, 0.010 mol). The reaction mixture was stirred at 5-10° C. for 2 hours. The ice-bath was removed and the stirring continued further at 30-35° C. for 1 hour. The reaction mixture was filtered and the filtrate evaporated under reduced pressure. Acetone (25 ml) was added to the residue and triturated. The solvent was decanted. This procedure was repeated twice with acetone (50 ml). Acetone after the third trituration was decanted and the residue dried under reduced pressure to obtain the product as white solid, 5.1 g, in 89% yield, Mp>165° C. (dec); MF: $C_{19}H_{24}F_2Na_2N_3O_8P$. Aqueous solubility at pH 7 was >200 mg/ml.

EXAMPLE 6

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester magnesium salt To a solution of phosphoric acid mono-(1-{4-[(S)-5-(acetylamino-methyl)-2-oxo-oxazolidin-3-yl]-2,6-difluorophenyl}-4-methoxymethyl-piperidin-4-yl)ester (5.0 g, 0.010mol) anhydrous methanol (50 ml) at 0-5° C., under argon, was added powdered anhydrous magnesium hydroxide (0.585 g, 0.010 mol) and water (5 ml) simultanously. The reaction mixture was stirred at 5-10° C. for 2 hours. The ice-bath was removed and the stirring continued further at 30-35° C. for 1 hour. The reaction mixture was filtered and the filtrate evaporated under reduced pressure. Acetone (25 ml) was added to the residue and triturated. The solvent was decanted. This procedure was repeated twice with acetone (50 ml). Acetone after the third trituration was decanted and the residue dried under reduced pressure to obtain the product as white solid, 4.9 g, in 92% yield, Mp>200° C. (dec); MF: $C_{19}H_{24}F_2MgN_3O_8P$. Aqueous solubility at pH 7 was ~2 mg/ml.

EXAMPLE 7

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester calcium salt To a solution of phosphoric acid mono-(1-{4-[(S)-5-(acetylamino-methyl)-2-oxo-oxazolidin-3-yl]-2,6-difluorophenyl}-4-methoxymethyl-piperidin-4-yl)ester (5.0 g, 0.010 mol) anhydrous methanol (50 ml) at 0-5° C., under argon, was added powdered anhydrous calcium acetate carbonate (1.58 g, 0.010 mol). The reaction mixture was stirred at 5-10° C. for 2 hours. The ice-bath was removed and the stirring continued further at 30-35° C. for 1 hour. The reaction mixture was filtered and the filtrate evaporated under reduced pressure. Acetone (25 ml) was added to the residue and triturated. The solvent was decanted. This procedure was repeated twice with acetone (50 ml). Acetone after the third trituration was decanted and the residue dried under reduced pressure to obtain the product as white solid, 5.0 g, in 91% yield, Mp >200° C. (dec); MF: $C_{19}CaH_{24}F_2N_3O_8P$. Aqueous solubility at pH 7 was ~0.5 mg/ml.

EXAMPLE 8

Phosphoric acid mono-(1-{4-[(S)-5-(acetylamino-methyl)-2-oxo-oxazolidin-3-yl]-2,6-difluorophenyl}-4-methoxymethyl-piperidin-4-yl)ester L-arginine salt To a solution of phosphoric acid mono-(1-{4-[(S)-5-(acetylamino-methyl)-2-oxo-oxazolidin-3-yl]-2,6-difluorophenyl}-4-methoxymethyl-piperidin-4-yl)ester (5.0 g, 0.010 mol anhydrous ethanol (50 ml) at 25-30° C., under argon, was added L-arginine (1.76 g, 0.010 mol). The reaction mixture was stirred at 80-85° C. for 0.5 h. Water (5 ml) was added to the reaction mixture and stirring continued further for 1 h at 80-85° C. The reaction mixture was filtered and the filtrate evaporated under reduced pressure. Acetone (25 ml) was added to the residue and triturated. The solvent was decanted. This procedure was repeated twice with acetone (50 ml). Acetone after the third trituration was decanted and the residue dried under reduced pressure to obtain the product as off-white solid, 6.1 g, 91% yield. Aqueous solubility at pH 7 was >200 mg/ml.

EXAMPLE 9

Phosphoric acid mono-(1-{4-[(S)-5-(acetylamino-methyl)-2-oxo-oxazolidin-3-yl]-2,6-difluorophenyl}-4-methoxymethyl-piperidin-4-yl)ester L-lysine salt To a solution of phosphoric acid mono-(1-{4-[(S)-5-(acetylamino-methyl)-2-oxo-oxazolidin-3-yl]-2,6-difluorophenyl}-4-methoxymethyl-piperidin-4-yl) ester (5.0 g, 0.010 mol) anhydrous methanol (50 ml) at 25-30° C., under argon, was added L-lysine (1.66 g, 0.010 mol). The reaction mixture was stirred at 25-30° C. for 0.5 h. Water (5 ml) was added to the reaction mixture and stirring continued further for 3 h at 25-30° C. The reaction mixture was filtered and the filtrate evaporated under reduced pressure. Acetone (25 ml) was added to the residue and triturated. The solvent was decanted. This procedure was repeated twice with acetone (50 ml). Acetone after the third trituration was decanted and the residue dried under reduced pressure to obtain the product as off-white solid, 6.1 g, 92% yield. Aqueous solubility at pH 7 was >200 mg/ml.

EXAMPLE 10

(S)—N-{3-[3,5-Difluoro-4-(4-(S)-2-tert-butoxycarbonylamino-methyl-4-methoxymethyl-piperidine-1-yl)phenyl]-2-oxo-oxazolidin-5-yl methyl}-acetamide To a solution of (3.81 g, 21.77 mmol) of N-Boc-glycine in dichloromethane (30 ml), under argon, was added DCC (4.2 g, 21.7 mmol), at 0-5° C. The resulting mixture was stirred for 0.5 h. To this solution, N—{(S)-3-[3,5-Difluoro-4-(4-hydroxy-4-methoxymethyl-piperidin-1-yl)-phenyl]-2-oxo-oxazolidin-5-ylmethyl}-acetamide (3 g, 7.2 mmol) and DMAP (2.52 g, 21.7 mmol) were added successively. The reaction mass stirred at room temperature for 15-20 hrs. The reaction mixture was filtered under suction and the residue further washed with additional dichlorometne (50 ml). The filtrate was washed with water (100 ml×2), dried over sodium sulfate, and the solvent evaporated under reduced pressure. The residue was chromatographed on a column of silica gel to obtain the product as a white, solid, 0.465 g, in 11% yield. Mass: 571 (M+1), MF=$C_{26}H_{36}F_2N_4O_8$.

EXAMPLE 11

2-Amino-acetic acid 1-{4-[(S)-5-(acetylamino-methyl)-2-oxo-oxazolidin-3-yl]-2,6-difluorophenyl}-4-methoxymethyl-piperidin-4-yl ester hydrochloride salt To (S)—N-{3-[3,5-Difluoro-4-(4-(S)-2-tert-butoxycarbonylamino-propionyl-4-methoxy-methyl-piperidin-1-yl)phenyl]-2-oxo-oxazolidin-5-yl methyl}-acetamide (150 mg), under argon was added a solution of HCl gas in IPA (2 ml) at room temperature. The resulting mixture was stirred for 16-18 hrs. The solvent was evaporated under reduced pressure and the residue triturated with diethyl ether. The ether layer was decanted. This procedure was repeated twice and the residual solid dried under vaccum to obtain the product as a highly hygroscopic solid, 90 mg, 68% yield. Aqueous solubility at pH 7 was >100 mg/ml.

EXAMPLE 12

2-Amino-acetic acid 1-{4-[(S)-5-(acetylamino-methyl)-2-oxo-oxazolidin-3-yl]-2,6-difluorophenyl}-4-methoxymethyl-piperidin-4-yl ester triflouroacetic acid salt To (S)—N-{3-[3,5-difluoro-4-(4-(S)-2-tert-butoxycarbonylamino-propionyl-4-methoxy-methyl-piperidine-1-yl) phenyl]-2-oxo-oxazolidin-5-yl methyl}-acetamide (150 mg), under argon was added 1 ml TFA in 2 ml dichloromethane at room temperature. The resulting mixture was stirred for 16-18 h. The solvent was evaporated under reduced pressure and the residue triturated with diethyl ether. The ether layer was decanted. This procedure was repeated twice and the residual solid dried under vaccum to obtain the product as a highly hygroscopic solid, 98 mg, 64% yield. Aqueous solubility at pH 7 was >100 mg/ml.

EXAMPLE 13

(S)—N-{3-[3,5-difluoro-4-(4-(S)-2-tert-butoxycarbonylamino-propionyl-4-methoxymethyl-piperidine-1-yl)phenyl]-2-oxo-oxazolidin-5-yl methyl}-acetamide To a solution of (4.1 g, 21.69 mmol) of N-Boc-alanine in dichloromethane (30 ml), under argon, was added DCC (4.2 g, 21.7 mmol), at 0-5° C. The resulting mixture was stirred for 0.5 h. To this solution, N—{(S)-3-[3,5-difluoro-4-(4-hydroxy-4-methoxymethyl-piperidin-1-yl)-phenyl]-2-oxo-oxazolidin-5-ylmethyl}-acetamide (3 g, 7.2 mmol) and DMAP (2.52 g, 21.7 mmol) were added successively. The reaction mass stirred at room temperature for 15-20 hrs. The reaction mixture was filtered under suction and the residue further washed with additional dichloromethane (50 ml). The filtrate was washed with water (100 ml×2), dried over sodium sulfate, and the solvent evaporated under reduced pressure. The residue was chromatographed on a column of silica gel to obtain the product as a white hygroscopic, solid, 0.5 g, in 12% yield. Mass: 585 (M+1), MF=$C_{27}H_{38}F_2N_4O_8$. Aqueous solubility at pH 7 was >100 mg/ml.

EXAMPLE 14

2-Amino-propionic acid 1-{4-[(S)-5-(acetylamino-methyl)-2-oxo-oxazolidin-3-yl]-2,6-difluorophenyl}-4-methoxymethyl-piperidin-4-yl ester hydrochloride salt To (S)—N-{3-[3,5-Difluoro-4-(4-(S)-2-tert-butoxycarbonylamino-propionyl-4-methoxy-methyl-piperidine-1-yl) phenyl]-2-oxo-oxazolidin-5-yl methyl}-acetamide (150 mg), under argon was added a solution of HCl gas in IPA (2 ml) at room temperature. The resulting mixture was stirred for 16-18 h. The solvent was evaporated under reduced pressure and the residue triturated with diethyl ether. The ether layer was decanted. This procedure was repeated twice and the residual solid dried under vaccum to obtain the product as a highly hygroscopic solid, 103 mg, 77% yield. Aqueous solubility at pH 7 was >100 mg/ml.

EXAMPLE 15

2-Amino-propionic acid 1-{4-[(S)-5-(acetylamino-methyl)-2-oxo-oxazolidin-3-yl]-2,6-difluorophenyl}-4-methoxymethyl-piperidin-4-yl ester triflouroacetic acid salt To (S)—N-{3-[3,5-Difluoro-4-(4-(S)-2-tert-butoxycarbonylamino-propionyl-4-methoxy-methyl-piperidine-1-yl) phenyl]-2-oxo-oxazolidin-5-yl methyl}-acetamide (150 mg), under argon was added 1 ml TFA in 2 ml dichloromethane at room temperature. The resulting mixture was stirred for 16-18 h. The solvent was evaporated under reduced pressure and the residue triturated with diethyl ether. The ether layer was decanted. This procedure was repeated twice and the residual solid dried under vaccum to obtain the product as a highly hygroscopic solid, 98 mg, 64% yield. Aqueous solubility at pH 7 was >100 mg/ml.

EXAMPLE 16

(S)—N-{3-[3,5-Difluoro-4-(4-(S)-2-carbobenzyloxyamino-3,3-dimethylpropionyl-4-methoxymethyl-piperidine-1-yl)phenyl]-2-oxo-oxazolidin-5-ylmethyl}-acetamide To a solution of N-cbz-valine (5.4 g, 21.69 mmol) in dichloromethane (30 ml), under argon, was added DCC (4.2 g, 21.7mmol), at 0-5° C. The resulting mixture was stirred for 0.5 h. To this solution, N—{(S)-3-[3,5-difluoro-4-(4-hydroxy-4-methoxymethyl-piperidin-1-yl)-phenyl]-2-oxo-oxazolidin-5-ylmethyl}-acetamide (3 g, 7.2 mmol) and DMAP (2.52 g, 21.7 mmol) were added successively. The reaction mass stirred at room temperature for 48 h. The reaction mixture was filtered under suction and the residue further washed with additional dichloromethane (50 ml). The filtrate was washed with water (100ml×2), dried over sodium sulfate, and the solvent evaporated under reduced pressure. The residue was chromatographed on a column of silica gel to obtain the product as a white, solid, 1.0 g, in 21% yield. Mass: 647 (M+1), MF=$C_{32}H_{40}F_2N_4O_8$. Aqueous solubility at pH 7 was >100 mg/ml.

EXAMPLE 17

2-Amino-3,3-dimethylpropionic acid 1-{4-[(S)-5-(acetylamino-methyl)-2-oxo-oxazolidin-3-yl]-2,6-difluorophenyl}-4-methoxymethyl-piperidin-4-yl ester methane sulfonic acid salt To a solution of (S)—N-{3-[3,5-difluoro-4-(4S-2-carbobenzyloxyamino-3,3-dimethyl-propionyl-4-methoxy-methyl-piperidine-1-yl)phenyl]-2-oxo-oxazolidin-5-ylmethyl}-acetamide (250 mg), in methanol (25 ml) was added methanesulphonic acid (37 mg) at room temperature. To this solution was added 0.05 g of 10% pd/C. The resulting mixture was hydrogenated at 30 Psi for 10 h. The catayst was filtered and the solvent evaporated under reduced pressure. The residue was triturated form ether twice to obtain a brown solid as product , 180 mg, 75% yield. Aqueous solubility at pH 7 was >100 mg/ml.

TEST EXAMPLE 1

Oral (15 mg/kg p.o) pharmacokinetic studies in male beagle dog: Male beagle dogs were dosed with (15 mg/kg p.o) the compound in water as a vehicle for oral and IV studies. 1% Tween suspension was used as a vehicle for (S)—N-{3-[3,5-difluoro-4-(4-methoxymethyl-4-hydroxypiperidine-1yl)-phenyl]-2-oxo-oxazolidin-5-ylmethyl}-acetamide oral studies whereas 25% Pharmasolve, 15% Ethanol and top up with 6% PEG 400 was used as a vehicle for (S)—N-{3-[3,5-difluoro-4-(4-methoxymethyl-4-hydroxypiperidine-1yl)-phenyl]-2-oxo-oxazolidin-5-ylmethyl}-acetamide study. For Example 3, Example 5, Example 6, Example 7 and Example 17, water was used as vehicle for oral and IV studies. For IV studies the compound was administered in a 15 min infusion. Blood samples were collected at time points of 0, 0.25, 0.50, 1.0, 1.5, 2.0, 3.0, 4.0, 5.0, 6.0, 8.0, 10.0, 12.0 and 24.0 h. Serum obtained from blood samples was used for HPLC & LC-MS/MS-based analysis. Serum samples were extracted by solid phase extraction technique using Water's OASIS HLB cartridges. An HPLC-Diode array detection system was used for analysis. Prepared samples were chromatographed on YMC-AM reversed phase column (150×4.6 mm ID; 5 µm) using gradient mobile phase acetate buffer (50 mmol ammonium acetate pH 6.6) acetonitrile, (for a representative compound of the invention) at a flow rate of 1 ml/min, measured at $\lambda_{max}$ 254 nm. Serum samples were precipitated by using acetonitrile. These samples were centrifuged at 10,000 rpm at 4° C. Resulting supernatant was injected onto LC-MS/MS. Prepared samples were chromatographed on a YMC-AM reversed phase column (150×4.6 mm ID; 5 µm) using isocratic mobile phase acetate buffer (50 mmol ammonium acetate pH 6.6) acetonitrile, (for a representative compound of the invention) at a flow rate of 1 ml/min, measured at $\lambda_{max}$ 254 nm. Independently prepared analytical standards and quality control samples were analyzed with each set of unknown samples.

TABLE 1

AUC and Cmax parameters by Oral route

| Compound | No. of dogs | Cmax (µg/ml) | AUC (µg · hr/ml) |
|---|---|---|---|
| Example-3 | 2 | 16.04 | 136.17 |
| Example-5 | 2 | 18.27 | 120.56 |
| Example-6 | 2 | 13.90 | 126.26 |
| Example-7 | 2 | 18.66 | 142.81 |
| Example-17 | 2 | 5.68 | 58.30 |
| (S)—N-{3-[3,5-difluoro-4-(4-methoxymethyl-4-hydroxy piperidine-1yl)-phenyl]-2-oxo-oxazolidin-5-ylmethyl}-acetamide | 9 | 12.24 | 109.32 |

TABLE 2

AUC and Cmax parameters by IV route

| Compound | No of dogs | Cmax (µg/ml) | AUC (µg · hr/ml) |
|---|---|---|---|
| Example-3 | 3 | 20.18 | 181.32 |
| (S)—N-{3-[3,5-difluoro-4-(4-methoxymethyl-4-hydroxy piperidine-1yl)-phenyl]-2-oxo-oxazolidin-5-ylmethyl}-acetamide | 5 | 22.64 | 165.13 |

While the present invention has been described in terms of its specific embodiments, certain modifications and equivalents will be apparent to those skilled in the art and are intended to be included within the scope of the present invention.

We claim:

1. Compounds having the structure of Formula I:

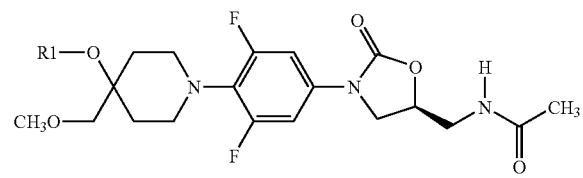

Formula I and their pharmaceutically acceptable salts,
wherein,
$R_1$ is
PO(OH)$_2$ or

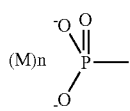

M is monovalent or divalent cation selected from Na$^+$, K$^+$, Mg$^{2+}$, Ca$^{2+}$;
n is 2 for monovalent cation or n is 1 for divalent cation.

2. The compound according to claim 1, wherein the pharmaceutically acceptable salts are sodium, potassium, magnesium, calcium, hydrochloride, acetate, trifluoroacetate, amino acid or salts of organic acids.

3. The compound of Formula I according to claim 1, wherein the compound is selected from the group consisting of:

Phosphoric acid mono-(1-{4-[(S)-5-(acetylamino-methyl)-2-oxo-oxazolidin-3-yl]-2,6-difluorophenyl}-4-methoxymethyl-piperidin-4-yl)ester;

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester di sodium salt;

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester di Potassium salt;

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester magnesium salt;

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester calcium salt;

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester arginine salt;

Phosphoric acid mono-(1-{4-[(S)-5-(acetylamino-methyl)-2-oxo-oxazolidin-3-yl]-2,6-difluoro-phenyl}-4-methoxymethyl-piperidin-4-yl)ester lysine salt.

4. The compound according to claim 1, wherein the compound comprises of, phosphoric acid mono-(1-{4-[(S)-5-(acetylamino-methyl)-2oxo-oxazolidin-3-yl]-2,6-difluorophenyl}-4-methoxymethyl-piperidin-4-yl) ester and pharmaceutically acceptable salts thereof.

5. A pharmaceutical composition comprising a therapeutically effective amount of a compound according to claim 1, optionally together with one or more pharmaceutically acceptable carriers, excipients or diluents.

6. The pharmaceutical composition according to claim 5, wherein the composition is administered parenterally or orally.

7. The method for treating microbial infections in a human or an animal, comprising administering to said animal or human, a therapeutically effective amount of a compound according to claim 1.

8. The method according to claim 7, wherein the microbial infections are caused by Gram-positive, Gram-negative bacteria, aerobic, anaerobic bacteria or atypical bacteria.

9. The method for treating microbial infections in an animal or a human comprising administering to animal or human, a pharmaceutical composition according to claim 5.

10. A process for preparing a compound as claimed in claim 1, the process comprising one or more of the following steps of:

a) Treating compound II with a suitable phosphorylating reagent in the presence of an activating agent, followed by oxidizing with an oxidizing agent to give compound of Formula III;

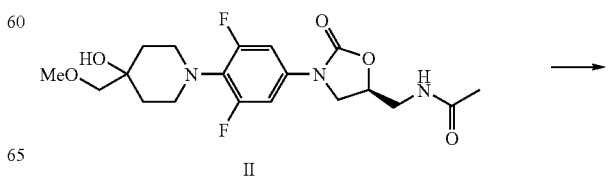

II

-continued

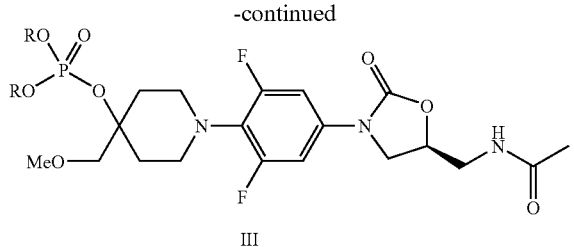

III b) Optionally, deprotecting the protecting groups to obtain compound of Formula IV;

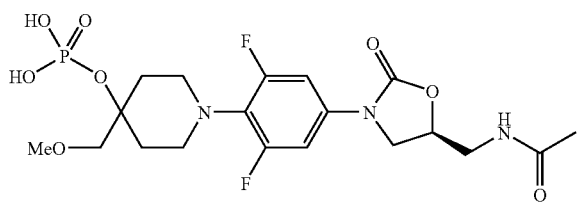

IV c) Optionally converting the compound of Formula IV into its corresponding salt.

11. The process of claim 10, wherein the phosphorylating reagent is selected from phosphoramidite or $PCl_3$.

12. The process of claim 11, wherein the phosphoramidite is selected from the group consisting of dibenzyl N,N,diisopropylphosphoramidite, dimethyl-N,N,diisopropylphosphoramidite, diethyl N,N,diisopropylpho sphoramidite, diallyl-N,N,diisopropylphosphoramidite, di-t-butyl N,N,diisopropylpho sphoramidite.

13. The process of claim 10, wherein the activating agent is selected from tetrazole, trimethyl silyl chloride, pyridinium hydrochloride, pyridinium trifluoroacetate, 4,5-dicyanoimidazole, pyridinium trifluomethanesulfonate, pyridinium acetate, pyridinium chloroacetate, pyridinium dichloro acetate, polyvinyl pyridinium hydrochloride, 2-amino-4,6-dimethyl pyrimidinium trifluoroacetate, imidazolium hydrochloride, imidazolium trifluoroacetate, aniline hydrochloride, p anisidine trifuoroacetate, o-toluidine hydrochloride, p-toluidine hydrochloride or phenanthrene trifluoroacetate.

14. The process of claim 10, wherein the oxidizing agent is selected from hydrogen peroxide (30%, 50% or 90%), urea hydrogen peroxide, peracetic acid, per trifluoroacetic acid, iodobenzene diacetate, m-chloroperbenzoic acid.

* * * * *